(12) United States Patent
Perra

(10) Patent No.: US 11,547,460 B2
(45) Date of Patent: Jan. 10, 2023

(54) VARIABLE-THICKNESS-HANDLE DRIVER INSTRUMENT

(71) Applicant: Warsaw Orthopedic, Inc., Warsaw, IN (US)

(72) Inventor: Joseph H. Perra, Wayzata, MN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 373 days.

(21) Appl. No.: 16/746,024

(22) Filed: Jan. 17, 2020

(65) Prior Publication Data
US 2021/0220034 A1  Jul. 22, 2021

(51) Int. Cl.
| | |
|---|---|
| *A61B 17/88* | (2006.01) |
| *A61B 17/70* | (2006.01) |
| *A61B 17/00* | (2006.01) |
| *B25B 15/00* | (2006.01) |
| *B25G 1/00* | (2006.01) |
| *B25G 1/10* | (2006.01) |

(52) U.S. Cl.
CPC ...... *A61B 17/8875* (2013.01); *A61B 17/7064* (2013.01); *A61B 17/7082* (2013.01); *A61B 17/7091* (2013.01); *A61B 2017/00424* (2013.01); *B25B 15/001* (2013.01); *B25B 15/004* (2013.01); *B25G 1/005* (2013.01); *B25G 1/105* (2013.01)

(58) Field of Classification Search
CPC ............ A61B 17/8875; A61B 17/7064; A61B 17/7082; A61B 17/8891; A61B 17/7091; A61B 2017/000424; A61B 17/8888; A61B 17/808; A61B 17/888; B25B 15/02; B25B 15/004; B25B 15/06; B25B 15/00; B25B 15/001; B25G 1/005; B25G 1/043; B25G 1/102; B25G 1/105; B25G 1/04

USPC .................. 606/104; 411/407–408
See application file for complete search history.

(56) References Cited

U.S. PATENT DOCUMENTS

| | | | | |
|---|---|---|---|---|
| 4,096,896 A | * | 6/1978 | Engel ..................... | B25B 15/00 81/177.85 |
| 5,450,775 A | * | 9/1995 | Kozak ................... | B25G 1/085 81/177.4 |
| 5,904,080 A | * | 5/1999 | Anderson ................ | B25F 1/02 81/439 |

(Continued)

FOREIGN PATENT DOCUMENTS

WO    2004032726 A2    4/2004

OTHER PUBLICATIONS

European Patent Office, 80298 Munich Germany, Application No. 151315.5-1 132, Applicant: Warsaw Orthopedic, Inc., dated Jun. 16, 2021.

*Primary Examiner* — Marcela I. Shirsat
(74) *Attorney, Agent, or Firm* — Sorell, Lenna & Schmidt, LLP

(57) ABSTRACT

An orthopaedic driving instrument including a first end portion, a second end portion opposite the first end portion, and a central portion, intermediate the first and second end portions, comprising a central section having an outer diameter representing a maximum outer diameter of the driving instrument. The first end comprises a first driving interface sized and shaped to, in operation of the instrument, engage a screw interface of a screw for applying torque to the screw. The second end comprises a second driving interface sized and shaped as the size and shape of the first driving interface.

14 Claims, 2 Drawing Sheets

(56) References Cited

U.S. PATENT DOCUMENTS

| | | | |
|---|---|---|---|
| 6,109,148 A * | 8/2000 | Anderson | B25B 15/008 |
| | | | 7/168 |
| 6,286,400 B1 * | 9/2001 | Anderson | B25G 1/043 |
| | | | 81/439 |
| 8,808,307 B2 * | 8/2014 | Robinson | A61B 17/7032 |
| | | | 606/104 |
| 10,383,675 B1 | 8/2019 | Cummins et al. | |
| 2008/0055889 A1 * | 3/2008 | Anderson | B25B 23/18 |
| | | | 362/119 |
| 2016/0296266 A1 | 10/2016 | Chandanson et al. | |
| 2018/0243022 A1 | 8/2018 | Marek et al. | |

* cited by examiner

VARIABLE-THICKNESS-HANDLE DRIVER INSTRUMENT

TECHNICAL FIELD

The present disclosure relates generally to medical devices for the treatment of musculoskeletal disorders, and more particularly to a driver instrument for use in a spinal or other orthopaedic surgery.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics.

As part of these surgical treatments, spinal constructs such as vertebral rods are often used to provide stability to a treated region. Rods redirect stresses away from a damaged or defective region while healing takes place to restore proper alignment and generally support vertebral members.

During surgical treatment, one or more rods and bone fasteners can be delivered to a surgical site. The rods may be attached via the bone fasteners to the exterior of two or more vertebral members. A surgeon may stabilize the vertebra by using a driver to insert the bone fasteners into the damaged vertebral body and attach the fasteners to one or more rods to help support and stabilize the damaged vertebra.

Driver instruments are used to thread a screw into patient vertebrae. The same or another driver instrument, or tightening tool, can also be used to complete threading into a screw head a set screw to lock the rod into the head.

A provisional drivers can be used to start threading of the set screw into the screw before a final tightening. Provisional drivers, being simpler and smaller, can provide a surgeon with greater tactile feedback, providing useful feel for how tight the set screw is becoming in threading down onto the rod.

Conventional drivers including provisional drivers have shortcomings including in some cases being one-sided, requiring a user to always ensure that a driver-end is oriented distally. Drivers including provisional drivers can also be difficult to grasp. This disclosure describes an improvement over these prior technologies.

SUMMARY

The systems of the present disclosure relate generally to a driver instrument for use in a spinal or other orthopaedic surgery, and more particularly to a provisional driver having a double-drive-ended driving having a variable-thickness handle.

In one aspect, the present disclosure provides an orthopaedic driving instrument including a first end portion, a second end portion opposite the first end portion, and a central portion, intermediate the first and second end portions, including a central section having an outer diameter representing a maximum outer diameter of the driving instrument. The first end includes a first driving interface sized and shaped to, in operation of the instrument, engage a screw interface of a screw for applying torque to the screw. The second end includes a second driving interface sized and shaped as the size and shape of the first driving interface.

In some cases, the first end portion has a first section having a first outer diameter, and the second end portion includes a second section having a second outer diameter equal to the first outer diameter.

The first end portion may have a first low-diameter section having an outer diameter, smaller than the first outer diameter, intermediate the maximum outer diameter of the central section and the first outer diameter of the first section, and the second end portion may have a second low-diameter section having an outer diameter, equal to the outer diameter of the outer diameter of the first low-diameter section, intermediate the maximum outer diameter of the central section and the second outer diameter of the second section.

In some case, the first end portion has a third section having a third outer diameter equal to the first outer diameter, the second end portion includes a fourth section having a fourth outer diameter equal to the first outer diameter, the first end portion includes a fifth section having a fifth section having a fifth outer diameter smaller than the first outer diameter intermediate the first section and the third section, and the second end portion includes a sixth section having a sixth section having a sixth outer diameter smaller than the first outer diameter intermediate the second section and the fourth section.

Outer surfaces of any of the surfaces, such as of each of the central, first, second, third, fourth, fifth, and sixth sections are in some embodiments textured.

The first end portion can include a first low-diameter section having an outer diameter, smaller than the first outer diameter, intermediate the maximum outer diameter of the central section and the first outer diameter of the first section, and the second end portion can include a second low-diameter section having an outer diameter, equal to the outer diameter of the first low-diameter section, intermediate the maximum outer diameter of the central section and the second outer diameter of the second section.

The first end portion may further include a third low-diameter section having an outer diameter, smaller than the first outer diameter, intermediate the first outer diameter and the third outer diameter, and the second end portion may include a fourth low-diameter section having an outer diameter intermediate the second outer diameter and the fourth outer diameter.

The instrument is in various embodiments symmetric, the first end portion having a first size and shape and the second end portion having a second size and shape matching the first size and shape.

The first driving interface is in some cases substantially identical to the second driving interface.

In another aspect, the disclosure provides an orthopaedic driving instrument having a first end portion, a second end portion opposite the first end portion; and a central portion, intermediate the first and second end portions, including a central section having an outer diameter representing a maximum outer diameter of the driving instrument. The first end in this aspect has a first driving interface, and the second end includes a second driving interface.

The first end portion may have a first section having a first outer diameter, and the second end portion may have a second section having a second outer diameter equal to the first outer diameter.

In some cases, the first end portion includes a first low-diameter section having an outer diameter, smaller than the first outer diameter, intermediate the maximum outer diameter of the central section and the first outer diameter of the first section. And the second end portion has a second low-diameter section having an outer diameter, equal to the outer diameter of the first low-diameter section, intermediate the maximum outer diameter of the central section and the second outer diameter of the second section.

The first end portion in various embodiments has a third section having a third outer diameter equal to the first outer diameter, the second end portion has a fourth section having a fourth outer diameter equal to the first outer diameter, the first end portion has a fifth section having a fifth section having a fifth outer diameter smaller than the first outer diameter intermediate the first section and the third section, and the second end portion has a sixth section having a sixth section having a sixth outer diameter smaller than the first outer diameter intermediate the second section and the fourth section.

In some embodiments, the first end portion has a first low-diameter section having an outer diameter, smaller than the first outer diameter, intermediate the maximum outer diameter of the central section and the first outer diameter of the first section, And the second end portion has a second low-diameter section having an outer diameter, equal to the outer diameter of the first low-diameter section, intermediate the maximum outer diameter of the central section and the second outer diameter of the second section.

Any of the instrument surfaces may be textured. And the instrument can be symmetric, the first end portion having a first size and shape and the second end portion having a second size and shape matching the first size and shape.

In still another aspect, the disclosures provides an orthopaedic driving instrument including a first end portion, a second end portion opposite the first end portion; and a central portion, intermediate the first and second end portions, having a central section having an outer diameter representing a maximum outer diameter of the driving instrument. The first end portion has a first section having a first outer diameter, the second end portion includes a second section having a second outer diameter equal to the first outer diameter. The first end portion also has a first low-diameter section having an outer diameter, smaller than the first outer diameter, intermediate the maximum outer diameter of the central section and the first outer diameter of the first section. And the second end portion has a second low-diameter section having an outer diameter, equal to the outer diameter of the first low-diameter section, intermediate the maximum outer diameter of the central section and the second outer diameter of the second section.

The instrument of this aspect can include any of the features described above in connection with the first wo aspect of the present disclosure.

The details of one or more aspects of the disclosure as set forth in the accompanying drawings and the description below. Other features, objects, and advantages of the techniques described in this disclosure will be apparent from the description and drawings, and from the claims.

DETAILED DESCRIPTION

The systems of this disclosure relate to an orthopaedic driver such as a provisional driver having a double-drive-ended driving having a variable-thickness handle.

Figure 1:
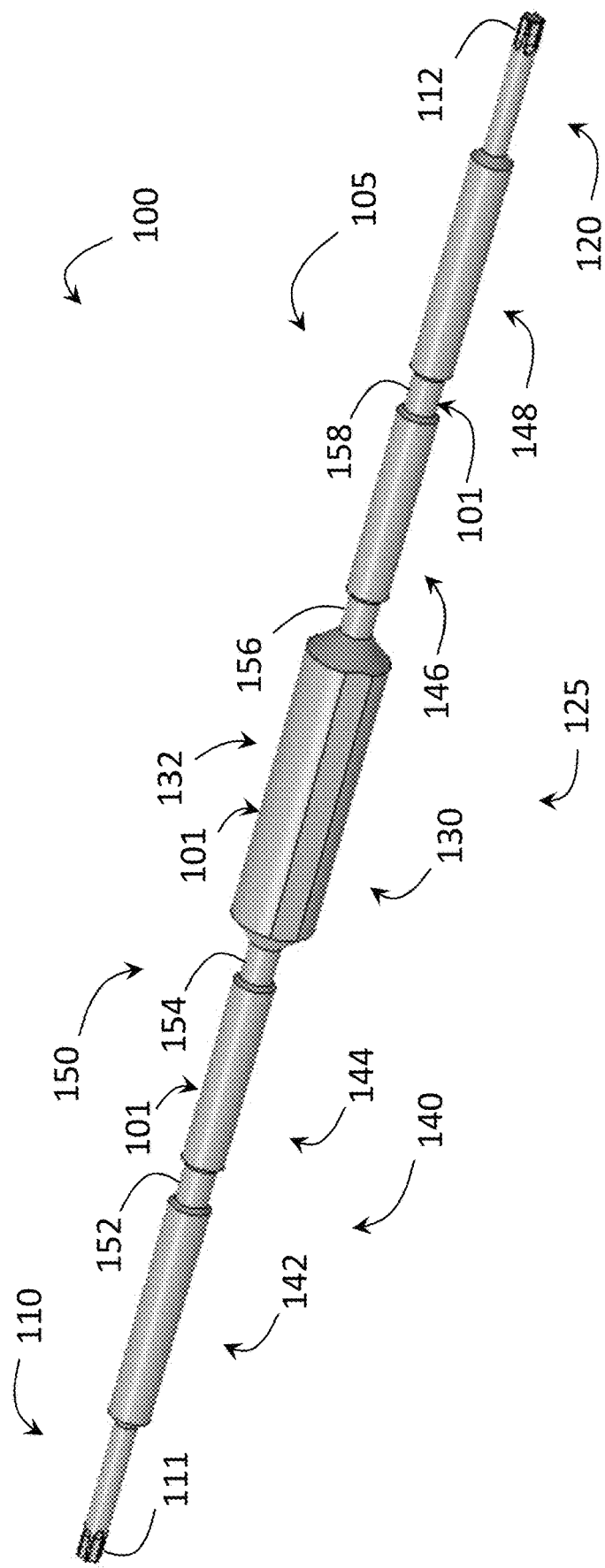
FIG. 1 is an isometric view of the multi-thickness-handle driver according to an embodiment of the present technology.
Figure 2:
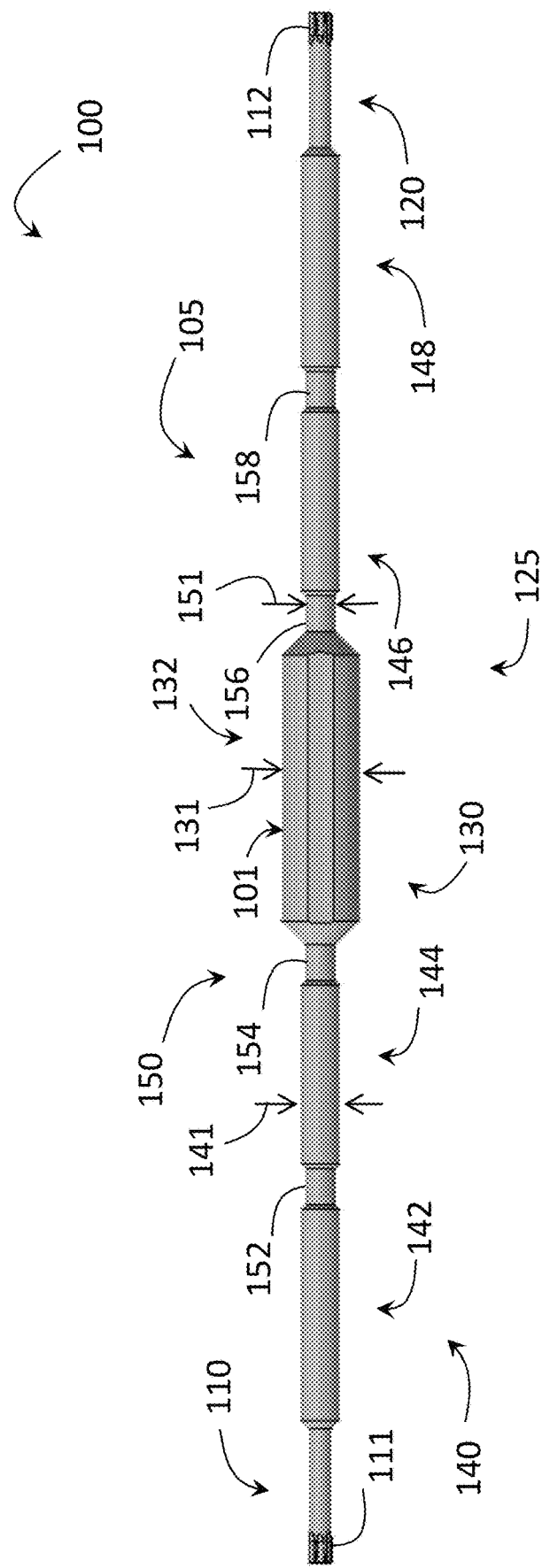
FIG. 2 is a side, or elevation, view of the driver of FIG. 1.

Turning now to the drawings, and more particularly to FIG. 1, a driver instrument according to an embodiment of the present disclosure is indicated generally by reference numeral 100.

The driver 100 can, as mentioned, be a provisional driver, and is not limited to spinal surgeries. The driver 100 may be used to provisionally and/or finally tighten a screw, and can be used for other orthopaedic surgeries, for instance.

The surgery may be a posterior spinal surgery, or anterior. The surgery can be minimally invasive, or mini-open surgery.

The driver 100 extends between opposing ends 110, 120. The ends 110, 120 include respective driving interfaces 111, 112. The driving interfaces 111, 112 can have any suitable configuration for engaging with the screw on which driver 100 is used.

The screw may include a set screw for threading into a screw head, of a bone screw, to lock a rod into the head. The screws and rod can be any conventional type and are thus, and to simplify the drawings, are not illustrated.

The driver 100 can be used to start threading of the set screw into the screw before a final tightening. Provisional drivers, being simpler and smaller, can provide a surgeon with greater tactile feedback, providing useful feel for how tight the set screw is becoming in threading down into the head and onto the rod.

The driver 100 in various embodiments includes, intermediate the ends 110, 120, a variable-thickness handle 125. The variable-thickness handle 125 may be referred to by other terms, such as a multiple-thickness handle, a variable-outer-diameter (OD) handle, a multiple-OD handle, a multi-thickness handle, or the like.

The driver 100 can be referred to as swizzle stick, and so by terms such as a variable-thickness driver or swizzle stick, multiple-thickness driver or swizzle stick, a variable-outer-diameter (OD) driver or swizzle stick, a multiple-OD driver or swizzle stick, a multi-thickness driver or swizzle stick, or the like.

In various embodiments, the variable-thickness handle 125 includes at least two portions or sections having differing thicknesses, or outer diameters (ODs). The sections include at least one thicker, or wider, section and at least one thinner section.

Surfaces of all driver sections are indicated by reference numeral 101. The surfaces can have one or more of any of various surface textures, including smooth, dimpled, ridged, irregular, non-smooth, textured, variable texturing, the like, or other.

The variable-thickness handle 105 includes at least one intermediate or central portion 130. The intermediate portion 130 includes an intermediate section 132 that in various embodiments represents a maximum OD or thickness 131 of the driver 100. The primary section 131 is in various cases perfectly or generally centered between the ends 110, 120 of the driver 110.

The intermediate section 131 can be referred to by any of various terms, such as a medial section, maximum-diameter section, a large-diameter section, a largest section, a central section, a middle section, a first section, a primary section, a primary or first grip or gripping section, the like, or other.

The variable-thickness handle 105 includes at least one narrower-handle, or second-handle, portion 140. The narrower-handle section 140 in the illustrated embodiment includes multiple narrower sections 142, 144, 146, 148. The narrower portion 140 has at least one OD or thickness 141. The section 140 can be referred to by any of various terms, such as a smaller-diameter section, a second section, a secondary section, a second grip or gripping section, the like, or other.

The smaller diameters of the narrower-handle section 140 are in some embodiments sized and shape to promote, facilitate, or allow certain placements of the instrument 100 with respect to implants that the instrument is used with. As an example, the smaller diameters of the narrower-handle section 140 are in some embodiments sized and shape to promote, facilitate, or allow collinear placement of the instrument 100 into a screw tubular-shaped screw. The smaller sections can be configured (e.g., made to have a geometry) that enables the user to place either driving interface 111, 112 into the tubular portion of such screw. This would not be possible if portions of the driver spaced too far from the intermediate portion 130 have the larger diameter of the intermediation section 132, as the larger diameter outside of the intermediate portion would obstruct the driver from entering the tubular portion of such screw, and so the interfaces 111, 112 could not reach the screw interface. As with all screws, the instrument 100 of the present technology promotes ease in starting such screws into the bone, and regarding this type, and other types of screws, can make placement easier or possible, depending on screw and narrower-section 140 dimensions.

In the illustrated embodiments, each section of the narrower portion 140 has identical or substantially the same thickness 141. In contemplated embodiments, two or more of the sections of the narrower portion 140 have different thicknesses.

The variable-thickness handle 105 in various embodiments includes at least one narrowest-handle portion 150. Use of the term narrowest, does not necessarily indicate that the sections of the narrowest portion 150 are strictly the narrowest sections of the primary portions 130, 140, 150, or of the driver 100. The description may recite such being the case explicitly. The section 150 can be referred to by any of various terms, such as a smallest-diameter section, a third section, a tertiary section, a third grip or gripping section, the like, or other.

For embodiments including the third, or narrowest, portion and section(s), the second, narrower portion or sections, can, in addition to any of the terms presented above for the second portion 140 or second section(s), be referred to as intermediate-thickness portion and sections, as an intermediate-diameter portion and sections, and as intermediate-OD portion and sections or the like.

The narrowest-handle section 150 in the illustrated embodiment includes multiple narrower sections 152, 154, 156, 158. The narrowest portion 150 has at least one OD or thickness 151. In the illustrated embodiments, each narrowest section of the narrowest portion 150 has identical or substantially the same thickness 151. In contemplated embodiments, two or more of the sections of the narrowest portion 150 have different thicknesses.

The variable thickness of the handle 125 facilitates robust handling by the surgeon, and anyone handling the driver 100. The user's fingers can better hold and manipulate, including applying torque using, the driver 100 with the sections having various thicknesses. The user's fingers can, when there are various thicknesses, naturally and better settle to gripping thicker and/or thinner areas of the driver 100.

The robust gripping enabled can include easy gripping using primarily or fully fingertips, or distal phalanges, allowing better feel and control in using the driver 100. Conventional drivers, being more cumbersome, can require use of more of a user's hand, such as requiring some or more use of the palm and other phalanges, proximal the distal phalanges.

In various applications, the driver 100 is configured, including by having the primary portion 130, to be able to be manipulated, including to apply torque, readily by a user using her palms, or a palm of one hand and distal phalanges of the other.

The increased, robust, grippability enabled by the design of the present technology can in some or all cases also enable a surgeon to apply a greater torque than she would be able to apply using conventionally-gripped drivers.

The increase maneuverability can also facilitate, with easier, faster rotation. So that the screw can be driven faster or with more speed.

It should be understood that various aspects disclosed herein may be combined in combinations other than the combinations presented specifically in the description and the accompanying drawings. It should also be understood that, depending on the example, certain acts or events of any of the processes or methods described herein may be performed in other sequence, added, merged, or left out altogether (e.g., all described acts or events may not be necessary to carry out the techniques).

In addition, while certain aspects of this disclosure are described as being performed by a single module or unit for purposes of clarity, it should be understood that the techniques of this disclosure may be performed by a combination of units or modules associated with, for example, a medical device.

Unless defined specifically otherwise herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An orthopaedic driving instrument comprising:
a first end portion;
a second end portion opposite the first end portion; and
a central portion, intermediate the first and second end portions, comprising a central section having an outer diameter representing a maximum outer diameter of the driving instrument;
wherein the first end comprises a first driving interface sized and shaped to, in operation of the instrument, engage a screw interface of a screw for applying torque to the screw;
wherein the second end comprises a second driving interface sized and shaped as the size and shape of the first driving interface;
wherein the first end portion comprises a first section having a first outer diameter;
wherein the second end portion comprises a second section having a second outer diameter equal to the first outer diameter;
wherein at least one of the first and second outer diameters has a circular cross-sectional configuration,
wherein the first end portion comprises a third section having a third outer diameter equal to the first outer diameter;
wherein the second end portion comprises a fourth section having a fourth outer diameter equal to the first outer diameter;
wherein the first end portion comprises a fifth section having a fifth outer diameter smaller than the first outer diameter intermediate the first section and the third section; and
wherein the second end portion comprises a sixth section having a sixth outer diameter smaller than the first outer diameter intermediate the second section and the fourth section.

2. The orthopaedic driving instrument of claim 1 wherein outer surfaces of each of the central, first, second, third, fourth, fifth, and sixth sections are textured.

3. The orthopaedic driving instrument of claim 1 wherein:
the first end portion comprises a first reduced-diameter section having an outer diameter, smaller than the first outer diameter, intermediate the maximum outer diameter of the central section and the first outer diameter of the first section; and
the second end portion comprises a second reduced-diameter section having an outer diameter, equal to the outer diameter of the first reduced-diameter section, intermediate the maximum outer diameter of the central section and the second outer diameter of the second section.

4. The orthopaedic driving instrument of claim 3 wherein:
the first end portion comprises a third reduced-diameter section having an outer diameter, smaller than the first outer diameter, intermediate the first outer diameter and the third outer diameter; and
the second end portion comprises a fourth reduced-diameter section having an outer diameter intermediate the second outer diameter and the fourth outer diameter.

5. The orthopaedic driving instrument of claim 1 wherein the instrument is symmetric, the first end portion having a first size and shape and the second end portion having a second size and shape matching the first size and shape.

6. The orthopaedic driving instrument of claim 1 wherein the first driving interface is identical to the second driving interface.

7. The orthopaedic driving instrument of claim 1 wherein the driving instrument extends along a longitudinal axis between the first end portion and the second end portion, the central portion having a length along the longitudinal axis that is greater than a length of the first driving interface along the longitudinal axis and a length of the second driving interface along the longitudinal axis.

8. An orthopaedic driving instrument comprising:
a first end portion;
a second end portion opposite the first end portion; and
a central portion, intermediate the first and second end portions, comprising a central section having an outer diameter representing a maximum outer diameter of the driving instrument;
wherein the first end comprises a first driving interface, and the second end comprises a second driving interface, the first driving interface being identical to the second driving interface;
wherein the first end portion comprises a first section having a first outer diameter;
wherein the second end portion comprises a second section having a second outer diameter equal to the first outer diameter;
wherein the first end portion comprises a third section having a third outer diameter equal to the first outer diameter;
wherein the second end portion comprises a fourth section having a fourth outer diameter equal to the first outer diameter;
wherein the first end portion comprises a fifth section having a fifth outer diameter smaller than the first outer diameter intermediate the first section and the third section; and
wherein the second end portion comprises a sixth section having a sixth outer diameter smaller than the first outer diameter intermediate the second section and the fourth section.

9. The orthopaedic driving instrument of claim 8 wherein:
the first end portion comprises a first reduced-diameter section having an outer diameter, smaller than the first outer diameter, intermediate the maximum outer diameter of the central section and the first outer diameter of the first section; and
the second end portion comprises a second reduced-diameter section having an outer diameter, equal to the outer diameter of the first reduced-diameter section, intermediate the maximum outer diameter of the central section and the second outer diameter of the second section.

10. The orthopaedic driving instrument of claim 8 wherein outer surfaces of the central, first, second, third, fourth, fifth, and sixth sections are textured.

11. The orthopaedic driving instrument of claim 8 wherein the instrument is symmetric, the first end portion having a first size and shape and the second end portion having a second size and shape matching the first size and shape.

12. An orthopaedic driving instrument comprising:
a first end portion;
a second end portion opposite the first end portion; and
a central portion, intermediate the first and second end portions, comprising a central section having an outer diameter representing a maximum outer diameter of the driving instrument;
wherein:
the first end portion comprises a first section having a first outer diameter;

the second end portion comprises a second section having a second outer diameter equal to the first outer diameter, wherein at least one of the first and second outer diameters has a circular cross-sectional configuration;

the first end portion comprises a first reduced-diameter section having an outer diameter, smaller than the first outer diameter, intermediate the maximum outer diameter of the central section and the first outer diameter of the first section; and the second end portion comprises a second reduced-diameter section having an outer diameter, equal to the outer diameter of the first reduced-diameter section, intermediate the maximum outer diameter of the central section and the second outer diameter of the second section, wherein the first end portion comprises a third section having a third outer diameter equal to the first outer diameter;

wherein the second end portion comprises a fourth section having a fourth outer diameter equal to the first outer diameter;

wherein the first end portion comprises a fifth section having a fifth outer diameter smaller than the first outer diameter intermediate the first section and the third section; and wherein the second end portion comprises a sixth section having a sixth outer diameter smaller than the first outer diameter intermediate the second section and the fourth section.

13. The orthopaedic driving instrument of claim 12 wherein:

the first end portion comprises a third reduced-diameter section having an outer diameter, smaller than the first outer diameter, intermediate the third outer diameter and the fifth outer diameter; and the second end portion comprises a fourth reduced-diameter section having an outer diameter, equal to the outer diameter of the first reduced-diameter section, intermediate the second outer diameter and the fourth outer diameter.

14. The orthopaedic driving instrument of claim 12 wherein outer surfaces of the central, first, second, third, fourth, fifth, and sixth sections are textured.

\* \* \* \* \*